(12) United States Patent
Bhatnagar et al.

(10) Patent No.: US 7,828,727 B2
(45) Date of Patent: Nov. 9, 2010

(54) MINIMALLY INVASIVE BONE MANIPULATION DEVICE AND METHOD OF USE

(75) Inventors: Mohit Bhatnagar, Potomac, MD (US);
Eric D. Major, Ashburn, VA (US);
Richard W. Woods, Catonsville, MD (US); Scott A. Jones, McMurray, PA (US); Robert A. Cripe, Costa Mesa, CA (US); Sanjog Kumar Mathur, Columbia, MD (US)

(73) Assignee: EBI, LLC, Parsippany, NJ (US)

( * ) Notice: Subject to any disclaimer, the term of this patent is extended or adjusted under 35 U.S.C. 154(b) by 486 days.

(21) Appl. No.: 11/763,113

(22) Filed: Jun. 14, 2007

(65) Prior Publication Data
US 2007/0239162 A1 Oct. 11, 2007

Related U.S. Application Data

(63) Continuation of application No. 10/861,865, filed on Jun. 7, 2004, now abandoned, which is a continuation-in-part of application No. 10/389,818, filed on Mar. 18, 2003, now abandoned.

(60) Provisional application No. 60/365,026, filed on Mar. 18, 2002.

(51) Int. Cl.
*A61B 1/32* (2006.01)
(52) U.S. Cl. .................. 600/203; 600/201; 600/206; 606/279
(58) Field of Classification Search .............. 606/90, 606/191, 198, 205–208, 282, 61, 69, 279; 600/201, 203, 206, 210, 216, 225; 623/17.16
See application file for complete search history.

(56) References Cited

U.S. PATENT DOCUMENTS

| 3,550,636 | A | 12/1970 | Hearne et al. |
|---|---|---|---|
| 3,800,788 | A | 4/1974 | White |
| 3,888,381 | A | 6/1975 | Russell, Jr. |
| 4,038,987 | A | 8/1977 | Komiya et al. |
| 4,276,659 | A | 7/1981 | Hardinge et al. |
| 4,294,251 | A | 10/1981 | Greenwald et al. |

(Continued)

FOREIGN PATENT DOCUMENTS

EP 0171176 2/1986

(Continued)

OTHER PUBLICATIONS

International Search Report for PCT/US03/08018 published with WO 03/079908 on Oct. 2, 2003.

(Continued)

*Primary Examiner*—Eduardo C Robert
*Assistant Examiner*—Christina Negrelli
(74) *Attorney, Agent, or Firm*—Harness, Dickey (57) ABSTRACT

A surgical apparatus. The apparatus includes a handle structure, a shaft structure coupled to the handle structure, and a spreading structure coupled to the shaft structure and movable between a compact and an expanded configuration. The apparatus includes a protective sheath of shape-recovery material. The protective sheath covers the entire spreading structure in a substantially form fitting manner in any configuration of the spreading structure including the compact configuration, the expanded configuration and any configurations therebetween.

21 Claims, 9 Drawing Sheets

U.S. PATENT DOCUMENTS

| | | | |
|---|---|---|---|
| 4,313,434 A | | 2/1982 | Segal |
| 4,338,925 A | | 7/1982 | Miller et al. |
| 4,357,716 A | | 11/1982 | Brown |
| 4,373,217 A | | 2/1983 | Draenert et al. |
| 4,399,814 A | | 8/1983 | Pratt, Jr. et al. |
| 4,429,691 A | | 2/1984 | Niwa et al. |
| 4,447,915 A | | 5/1984 | Weber et al. |
| 4,462,394 A | | 7/1984 | Jacobs |
| 4,488,549 A | | 12/1984 | Lee et al. |
| 4,562,598 A | | 1/1986 | Kranz et al. |
| 4,576,152 A | | 3/1986 | Muller et al. |
| 4,627,434 A | | 12/1986 | Murray |
| 4,645,503 A | | 2/1987 | Lin et al. |
| 4,697,584 A | | 10/1987 | Haynes |
| 4,705,519 A | | 11/1987 | Hayes et al. |
| 4,888,024 A | | 12/1989 | Powlan |
| 4,917,702 A | | 4/1990 | Scheicher et al. |
| 4,969,888 A | | 11/1990 | Scholten et al. |
| 5,059,193 A | | 10/1991 | Kuslich |
| 5,108,404 A | | 4/1992 | Scholten et al. |
| 5,113,846 A | | 5/1992 | Hiltebrandt et al. |
| 5,235,966 A | * | 8/1993 | Jamner .................. 600/204 |
| 5,383,932 A | | 1/1995 | Wilson et al. |
| 5,656,012 A | * | 8/1997 | Sienkiewicz .............. 600/204 |
| 5,662,657 A | | 9/1997 | Carn |
| 5,755,661 A | | 5/1998 | Schwartzman |
| 5,766,178 A | | 6/1998 | Michielli et al. |
| 5,782,917 A | | 7/1998 | Carn |
| 5,849,014 A | | 12/1998 | Mastrorio et al. |
| 5,861,043 A | | 1/1999 | Carn |
| 5,879,403 A | | 3/1999 | Ostiguy et al. |
| 5,888,196 A | | 3/1999 | Bonutti |
| 5,928,239 A | | 7/1999 | Mirza |
| 5,935,169 A | | 8/1999 | Chan |
| 5,993,473 A | | 11/1999 | Chan et al. |
| 5,997,580 A | | 12/1999 | Mastrorio et al. |
| 6,139,508 A | | 10/2000 | Simpson et al. |
| 6,221,107 B1 | | 4/2001 | Steiner et al. |
| 6,227,860 B1 | | 5/2001 | Hobo et al. |
| 6,241,734 B1 | | 6/2001 | Scribner et al. |
| 6,251,141 B1 | | 6/2001 | Pierson, III et al. |
| 6,273,916 B1 | | 8/2001 | Murphy |
| 6,309,349 B1 | | 10/2001 | Bertolero et al. |
| 6,319,252 B1 | | 11/2001 | McDevitt et al. |
| 6,322,500 B1 | | 11/2001 | Sikora et al. |
| 6,354,994 B1 | | 3/2002 | Rullo et al. |
| 6,354,995 B1 | | 3/2002 | Hoftman et al. |
| 6,358,266 B1 | | 3/2002 | Bonutti |
| 6,582,451 B1 | | 6/2003 | Marucci et al. |
| 2001/0049531 A1 | | 12/2001 | Reiley et al. |
| 2002/0013600 A1 | | 1/2002 | Scribner et al. |
| 2002/0022856 A1 | | 2/2002 | Johnson et al. |
| 2002/0026195 A1 | | 2/2002 | Layne et al. |
| 2002/0032447 A1 | | 3/2002 | Weikel et al. |

FOREIGN PATENT DOCUMENTS

| | | |
|---|---|---|
| WO | WO-8303193 | 9/1983 |
| WO | WO-0213700 | 2/2002 |
| WO | WO-03079908 A1 | 10/2003 |

OTHER PUBLICATIONS

PCT International Preliminary Examination Report for PCT/US03/08018 dated Sep. 18, 2004.
U.S. Appl. No. 10/389,818 Office Action mailed Jun. 28, 2005.
U.S. Appl. No. 10/389,818 Office Action mailed Dec. 22, 2005.
U.S. Appl. No. 10/389,818 Advisory Action mailed Apr. 10, 2006.
U.S. Appl. No. 10/861,865 Office Action mailed Dec. 11, 2006.
U.S. Appl. No. 10/861,865 Office Action mailed Apr. 13, 2007.

* cited by examiner

MINIMALLY INVASIVE BONE MANIPULATION DEVICE AND METHOD OF USE

CROSS-REFERENCE TO RELATED APPLICATIONS

This application is a continuation of U.S. patent application Ser. No. 10/861,865 filed on Jun. 7, 2004, which is a continuation-in-part of U.S. application Ser. No. 10/389,818, filed Mar. 18, 2003 which claims priority to U.S. Provisional Application Ser. No. 60/365,026 filed Mar. 18, 2002. The disclosures of the above applications are incorporated herein by reference.

INTRODUCTION

The present teachings relate to a surgical apparatus for use in orthopedic surgery procedures. Particularly, the present teachings relate to the treatment of traumatic, pathogenic, or osteoporotic bone conditions of human and other animal body systems and, more particularly, to a novel apparatus and method for manipulating the vertebral body through a less invasive, percutaneous, surgical approach.

Surgical procedures frequently require that after surgical entry has been made the tissues within the patient's body must be expanded away from the surgical point of interest in order to provide better access and visibility for the surgeon. Various surgical devices have been developed to assist the surgeon to displace tissue and expand the interior cavities of the body during both open surgical procedures and less invasive surgical procedures.

Surgical procedures vary dramatically depending upon the region of the body involved and the purpose of the surgery. The design and the use of surgical instruments are equally specialized and instruments which seemingly are intended for similar purposes can be significantly different from one another depending upon the exact nature of the surgery. The use of retractors to expand an opening or create a space to facilitate access for the surgeon during the performance of a surgical procedure is well known in the art. It is, however, often the case that one tissue retractor designed for use in a particular surgical procedure will be completely unsuitable for retraction of tissue in a different type of surgery.

Conventional surgical procedures, which have been employed to alleviate vertebral compression failures, involve major invasive surgical techniques with all of the possible negative consequences. The close proximity of the spinal cord to damaged sections of a vertebra, which are in need of surgical repair, presents a particularly hazardous situation for the patient and increases the challenge for the surgeon tremendously. Recent surgical innovations have been made that provide a means of reinforcing damaged vertebra by the injection of bone cement into the vertebral body. However, in patients suffering from crippling effects of osteoporosis and the possibility of compression fractures of multiple vertebrae, there remains a need for an effective and safe way to distract the vertebral endplates so as to alleviate the compressed disposition of the vertebral body. Such a specialized requirement dictates the need for a specialized tissue expansion device. Numerous tissue expansion devices have been developed for different surgical procedures including tissue retractor used to expand a body wall entry incision. For nearly a century such retractors with one or more specialized modifications have been used to meet the particular requirements for body wall incision expansion in different surgical procedures. Other tissue manipulators or expanders include an inflatable balloon as the mechanical device to expand the skin around a surgical entry site. Balloon-type expansion devices are uncontrolled and multi-directional, which can lead to undesirable expansion of the bone or bone fragments being displaced in unwanted directions Conventionally used tissue expansion devices are each configured to precisely meet the specific needs for particular surgical procedures and, as such, are not readily (if at all) adaptable to meet the needs of a different surgical procedure.

Conventional devices share the common problem of possibly suffering mechanical interference or fouling of the mechanism when tissue or bone come into contact with the internal mechanism of the devices. Such fouling of the mechanism by involvement with tissue or bone during the insertion process, expansion process, or the retraction process can severely limit the effectiveness of such a device. Each possibility presents a unique problem for the surgeon using an unprotected manipulating device, such as, for example, if the mechanism becomes fouled or occluded during the insertion process, it may fail to operate once it is properly in place. Similarly, it is possible that during operation of the expansion mechanism, the exposed mechanism can become occluded and thus limit or fully stop the expansion process. Finally, if the unprotected mechanism is fouled or hung-up on tissue or bone during the retraction or removal process, the removal may be impeded so as to require additional surgical procedures to successfully extract the device.

The present teachings provide a less invasive surgical device, which can be precisely controlled by the surgeon to expand tissue and transmit sufficient force to manipulate bone in a selected direction or, if desired, in multiple directions. Further, the present teachings provide a device that protects the mechanism from unwanted contact with surrounding tissues, where such contact might result in occlusion or fouling of the mechanism such that the function of the device is compromised.

SUMMARY

The present teachings generally provide a device designed for use as a less invasive means of controllably manipulating a damaged bone, and in particular a patient's vertebra to create a void therein so as to enable a surgeon to accomplish a surgical procedure while providing a protective member on the mechanism to avoid undesirable contact with surrounding tissue and bone.

The present teachings provide a surgical apparatus that includes a handle structure, a shaft structure coupled to the handle structure, and a spreading structure coupled to the shaft structure and movable between a compact and an expanded configuration. The apparatus includes a protective sheath of shape-recovery material. The protective sheath covers the entire spreading structure in a substantially form fitting manner in any configuration of the spreading structure including the compact configuration, the expanded configuration and any configurations therebetween.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

The apparatus and method of the present teachings can be adapted for use in a variety of surgical procedures which require precise tissue manipulation by a surgeon. The following description and associated FIGS. 1-11C are provided as non-limiting examples of the present teachings, which is defined with particularity only by the claims of the present teachings.

As shown in FIGS. 1-10, a tissue manipulation device (10) is provided. In one aspect, the device is configured to be particularly well-suited to the manipulation of bone in a subject. By way of example, the device (10), as best shown in FIGS. 1-9, includes three portions or assemblies which can be integrally formed or separately fabricated prior to being joined to form the device (10).

The three assemblies, which together form the device (10), include a handle assembly (12), a shaft assembly (14) and a spreading assembly (16). A proximal end (18) of the shaft assembly (14) is connected to the handle assembly (12) and a distal end (20) of the shaft assembly (14) is connected to the spreader assembly (16).

As earlier indicated, these three assemblies (12, 14, 16) can be integrally formed or, alternatively, can be individually formed and then connected to form the whole device (10). It is also within the concept of the present teachings for the one or more of the assemblies to be releasably connected one to the other.

In an embodiment where the three assemblies (12, 14, 16) are formed and subsequently permanently connected one to the other, the connections may be of any character known for connecting parts of a whole into one unit, to include, for example: gluing, soldering, welding, mechanically joining by rivets or screws or the like or any other means for permanently connecting parts one to the other.

If the three assemblies (12, 14, 16) are releasably attached one to the other, any releasable attachment means known can be used, to include, for example: snap fittings, bayonet fittings, luer lock fittings, threaded fittings, cotter-pin connections, plug and socket connections, or any other releasable attachment means. If the device (10) is integrally formed, any manufacturing process known can be employed, to include extrusion molding, die-casting, tooling, or any other means of fabricating such a device.

When the device (10) is configured to permit releasable attachment of the three assemblies (12, 14, 16) to each other, it is possible for the user to attach alternative embodiments of any of the three individual assemblies (12, 14, 16). This feature of the present teachings permits each of the three assemblies (12, 14, 16) to separately have specifically designed embodiments that are configured for very specific uses or for individual preferences of the using surgeon. Thus, one embodiment of the device (10) enables the user to customize the combination of the three assemblies (12, 14, 16) to meet the particular requirements for a specific surgical procedure.

Figure 1:
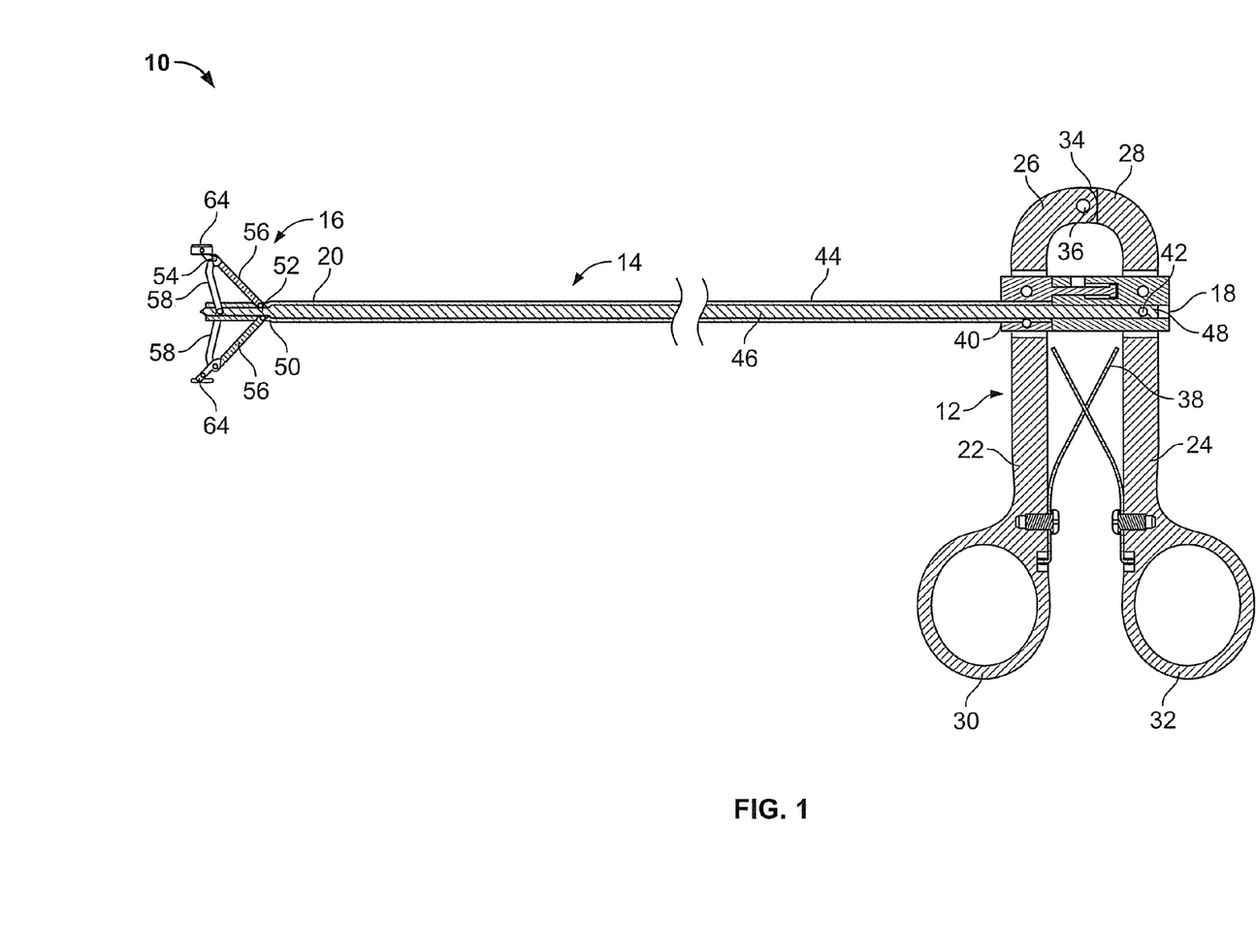
FIG. 1 is a cross-sectional plan view of a first embodiment of the device of the present teachings, which shows the mechanism configured in an expanded position.
Figure 2:
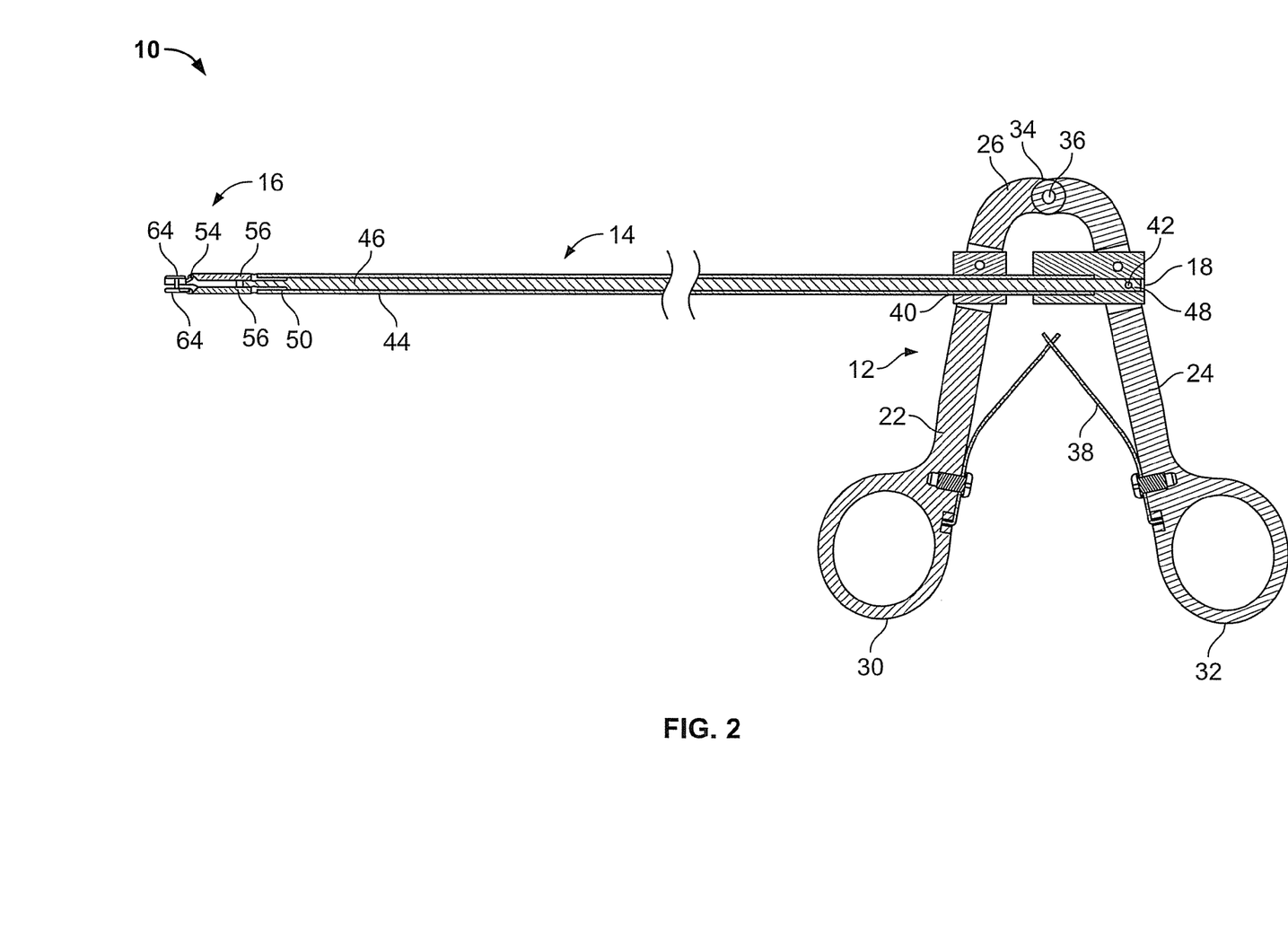
FIG. 2 is a cross-sectional plan view of a first embodiment of the device of the present teachings, which shows the mechanism configured in a closed position.
Figure 3:
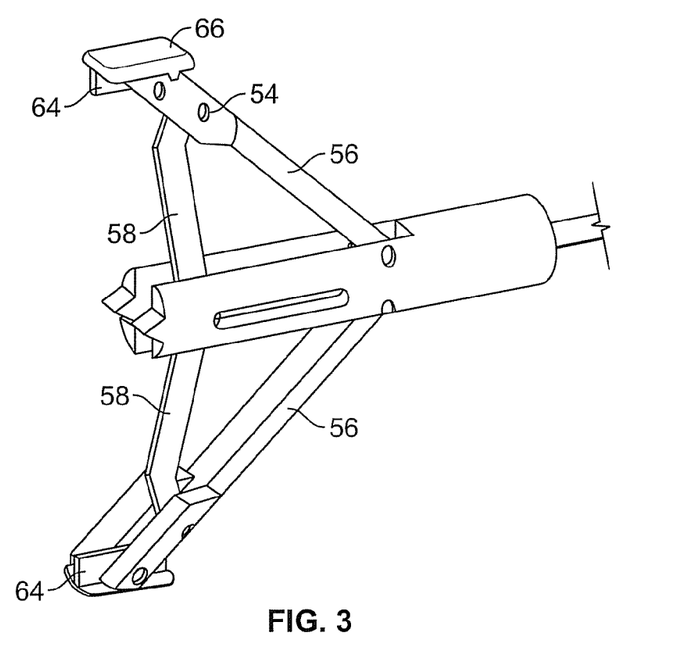
FIG. 3 is an isometric view of the mechanical detail of the modular spreading assembly of a second embodiment of the present teachings in the expanded position.
Figure 4:
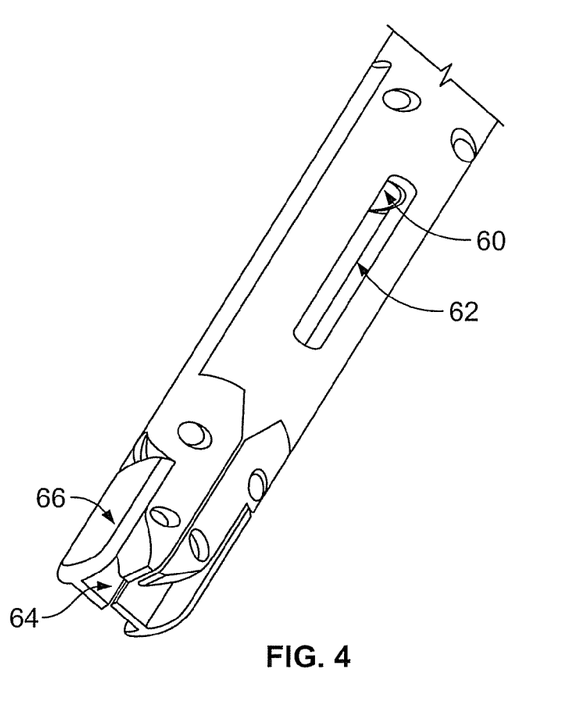
FIG. 4 is an isometric view of the mechanical detail of the modular spreading assembly of the embodiment of the present teachings of FIG. 3 shown in the closed position.
Figure 5A:
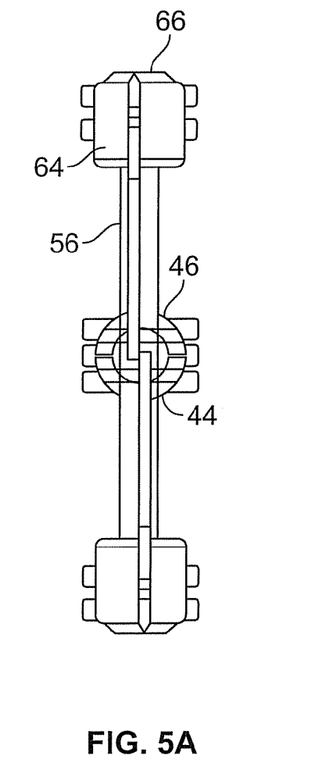
FIGS. 5A-C show plan, top and end views of the modular spreading assembly of the embodiment of the present teachings shown in FIGS. 3-4.
Figure 5B:
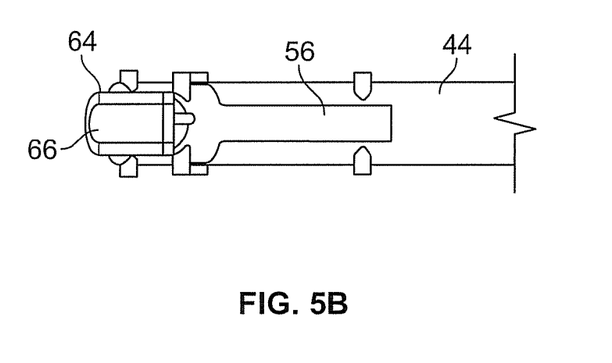
Figure 5C:
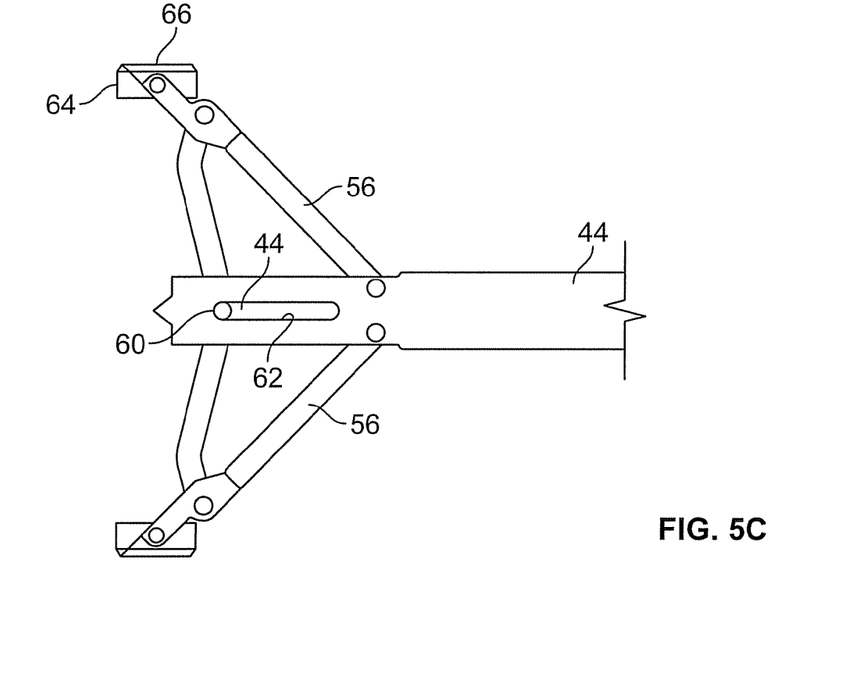

As best shown in FIGS. 1-2, the handle assembly (12) can be configured to operate as a scissor-like embodiment so as to provide ease of handling by a user during operation of the device (10). FIG. 1 provides a depiction of the scissor-like embodiment of the handle assembly (12) in the device-open configuration while FIG. 2 depicts this embodiment in a device-closed configuration. It is within the concept of the present teachings to reverse the operable effect of the handle positions shown in FIGS. 1 and 2 without departing from the concept of the present teachings. The scissor-like embodiment of the handle assembly (12) depicted in FIGS. 1 and 2 can include a first handle member (22) and a second handle member (24), each handle member (22, 24) having respectively a connecting end (26, 28) and a gripping end (30, 32).

Each of the connecting ends (26, 28) is movably connected one to the other by a handle member connector (34). In one aspect, the handle member connector (34) is configured as a handle member pivot pin (36) although the handle member connector (34) can be configured as rotationally engaged portions of the first and second handle members (22, 24). Thus, the handle member connector (34) can be configured to include a pivot pin (36), a rotating ball-and-socket joint, a rotating rim-and-groove joint, or any other connection design which permits the connecting ends (26, 28) of the first and second handle members (22, 24) to be connected in a moveable relationship one to the other. The first and second handle members (22, 24) can be biased into a closed or open relationship one to the other by a biasing member (38), which can be releasably attached to facilitate repair and replacement.

The handle members (22, 24) can define an actuating arm portal (40) which provides for an arm anchor (42) defined within the second handle member (24). The portion of the portal (40) defined through the first handle member (24) can be sized and configured to hold and restrict the movement of an actuating arm sleeve (44). The shaft assembly (14) includes the actuating arm sleeve (44) and the actuating arm (46). The actuating arm sleeve (44) can be sized and configured to permit sliding passage of the actuating arm (46). The actuating arm (46) at its proximal end (48) can be releasable attached to the actuating arm anchor (42). Both the actuating arm (46) and the actuating arm sleeve (44) are configured to be in a sliding relationship, one within the other, and to be of a respective fixed length such that the actuating arm (46) can slide to a position which extends beyond the distal end (50) of the sleeve (44).

Attached at the distal end of the actuating arm (52) is a spreading assembly (16). The spreading assembly (16) can be sized and configure to fit within the sleeve (44) when the actuating arm (46) is fully withdrawn into the sleeve (44). The spreading assembly (16) can be releasable from the actuating arm to permit the surgeon to insert the spreading assembly into a bone, actuate the spreading assembly into an expanded position, and, if desired, disconnect the spreading assembly so as to permit it to be left within the bone. This optional releasable feature of the spreading assembly (16) also permits the device to be configured with different sizes and configurations of spreading assembly prior to use.

The spreading assembly (16), as best seen in FIGS. 3, 4, and 5A-C, can be configured to include at least one extending arm (56) that can be in pivotal relationship at one end with the actuating sleeve (44). Any sufficiently strong material compatible for use in surgical instruments can be used in the manufacture of the device. The extending arm (56) can be manufactured of a rigid material to provide strength and reliable, consistent performance during operation. Conventional spreaders, which can include flexible sleeves, are incapable of providing the even, consistent force during operation that is essential for safely manipulating bone material. This especially important when manipulating the end plates of a vertebral body. At least one bracing member (58) is rotationally attached at one end to the actuating arm (46) and rotationally attached at the other end to the proximal end of the extending arm (56). Due to the operational requirement of manipulating bone, the bracing member can be manufactured of rigid material, however any material suitable for use in surgical instruments can be used if sufficiently strong. In operation, when the actuating arm (46) is extended distally beyond the confines of the sleeve (44), the bracing member (58) serves to exert a force on the extending arm (56) so as to force the spreading assembly into an open position. A locking mechanism can be provided so as to releasably lock the spreading assembly into position. This locking mechanism can be configured as a notch, slot, or other like means to fix the spreading assembly into an open position. The locking mechanism can be selectively locked or unlocked.

To facilitate smooth operation of the spreading assembly (16), a guide bar (60) sized and configured to slidably move with the confines of a guide slot (62) can be provided. The guide slot (62) can define the forward most and reward most movement of the guide bar (60) and in so doing control the degree of extension of the spreading assembly in operation. The guide slot (62) can thus be sized to control the amount of extension possible for the spreading assembly (16). The distal most portion of the extending arm (56) can be provided with a base plate (64), which can be pivotally attached thereto. The base plate (64) is sized and configured to provide a contact surface (66) that in operation is brought into contact with the bone to be manipulated. This contact surface (66) can provide a protective element to distribute the pressure exerted by spreading assembly across a broader surface of the bone being manipulated.

To provide visual feedback to the surgeon, the device (10) can be manufactured such that at least a portion of the device is radiopaque. It is within the concept of the present teachings that only select portions of the device (10), such as, for example, the contact surface (66) or the base plate (64) are manufactured or treated to include radiopaque material. Any method known in the art to manufacture or treat the device (10) so as to have a radiopaque quality can be employed without departing from the general concept of the present teachings.

Figure 6:
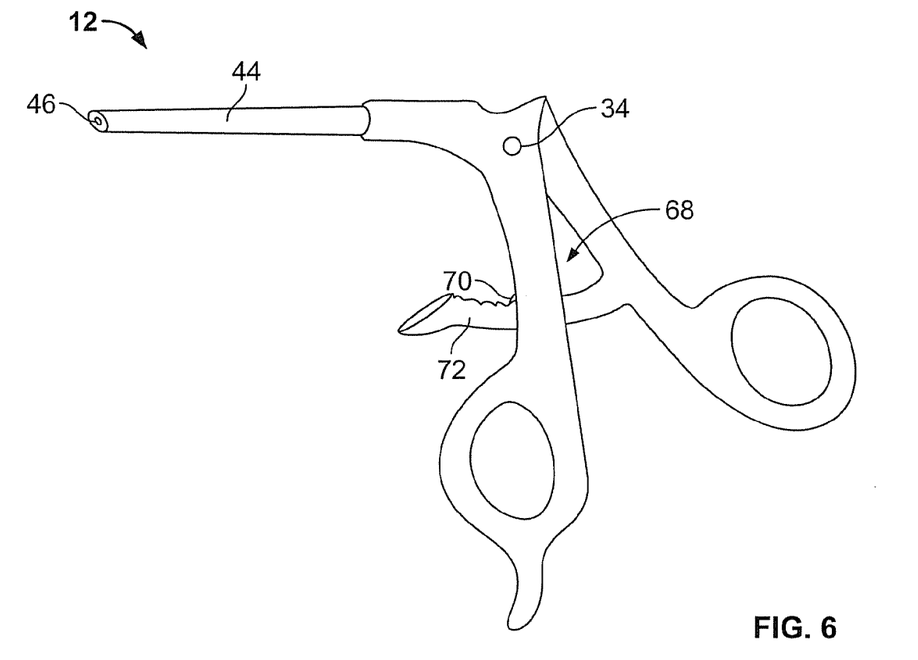
FIG. 6 is an isometric view of an alternative handle assembly of the present teachings.

The first embodiment of the present teachings described above illustrates an aspect of the present teachings. It is, however, within the scope of the present teachings to configure the device (10) with a wide variety of handle assemblies (12) that would serve to actuate the device by movement of the actuating arm (46) with the actuating arm sleeve (44). Another non-limiting example of an alternative handle assembly (12) is shown in FIG. 6. This alternative handle assembly (12) can be configured similar to the scissor-like embodiment shown in FIGS. 1-2 with the additional feature of a handle locking assembly, generally shown at (68). The handle locking assembly (68) can be provided with a locking catch (70) similar to that typically found on a hemostat instrument. The locking catch (70) can be employed with a handle locking arm (72) that is configured for releasably locking the handle assembly (12) to a desired open, partially open, or closed position as desired by the using surgeon.

Figure 10:
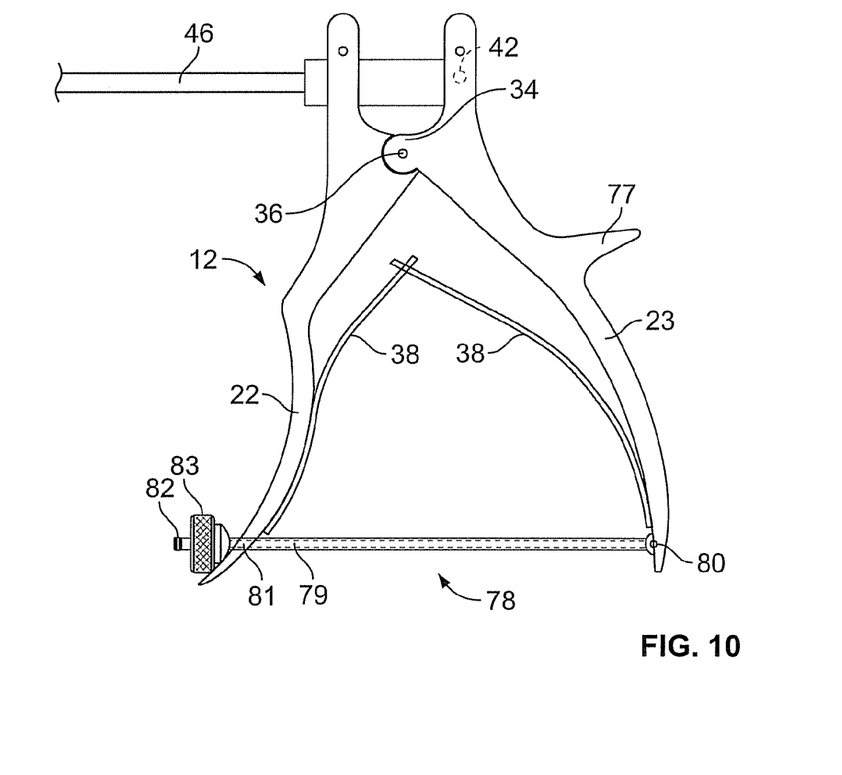
FIG. 10 shows another alternative embodiment of the handle assembly of the present teachings.

Another embodiment of the present teachings can include an alternative handle assembly as shown in FIG. 10, which generally includes the basic features of the handle assemblies discusses above, that is, opposing first and second handle members (22, 23), a handle member connector (34) and pivot pin (36), an actuating arm anchor (42) for securing the distal end of the actuating arm (46), and at least one biasing member (38). The alternative handle assembly shown in FIG. 10 also includes the additional feature of a grip stabilizing member (77), against which the users' first thumb joint can rest during operation, and a controlled compression assembly, generally shown at (78), which provides a means for the user to fine-tune control the compression of the two handle members. The controlled compression assembly (78) includes a threaded compression shaft (79) that is rotatably connected to the second handle member (23) by a shaft securing member (80). The threaded compression shaft (79) slidably extends through a compression shaft bore (81) defined in the first handle member 22 and terminates in a manual controller stop (82). The manual controller stop (82) acts to limit the extreme movement of the manual controller (83), which is correspondingly-threaded and disposed around the threaded compression shaft (79). In one aspect of this handle assembly, the manual controller (83) is configured as a thumb wheel for ease of operation. In operation, the user can manually compress the handle members (22, 23) together and, if desired, move or thread the manual controller (83) along the threaded compression shaft (79) to a position that holds the two handle members (22, 23) in the selected position relative one to the other. Alternatively, the handle members can be moved toward or away from each other by simply manually turning the manual controller (83) so as to tighten or loosen the control member against the outward bias of the first handle member (22), the bias being provided by the at least one biasing member (38).

Figure 11A:
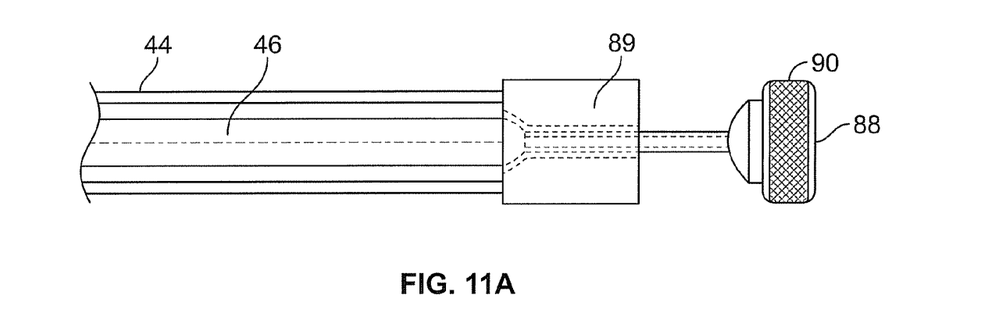
FIGS. 11A-11C show three non-limiting, alternative examples of a knob-type handle assembly for use with the present teachings.
Figure 11B:
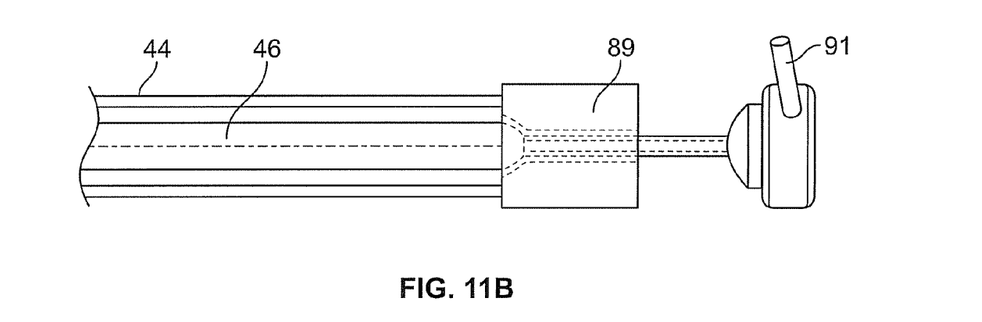
Figure 11C:
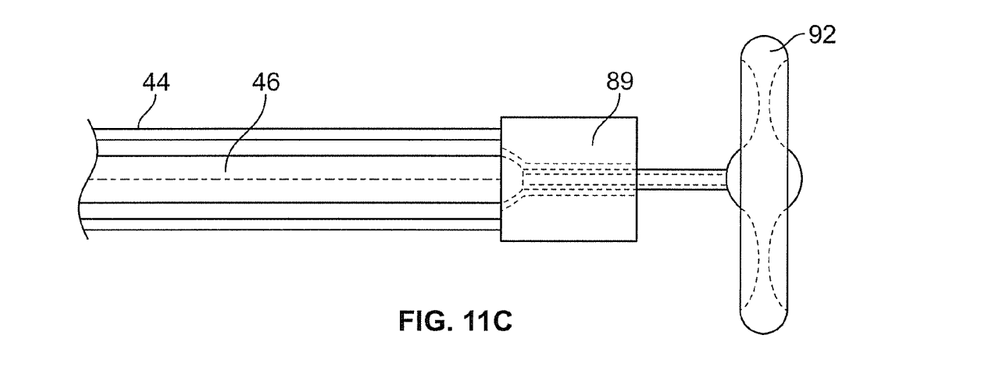

Without departing from the general concept of the present teachings, the handle assembly (12) can be provided as a simple grip and control mechanism, such as a knob, in place of a multi-membered squeeze-actuated handle. As best shown in FIGS. 11A-11C, This alternative knob configuration can be provided as a simply configured control knob (88), which can be provided in any form as is known in the art, to include, for example a rotationally attached, longitudinally aligned knurled knob (88) employing a screw-type actuator (89) to advance or retract the actuating arm (46) within the sleeve (44); the knob being knurled (90) or equipped with one or more radially extending side grips (91), or equipped with a circumferentially disposed gripping ring (92), as is commonly used in the art, for example as a common handle for a water faucet valve. Regardless of the configuration selected, the knob (88) embodiment of the handle assembly provides for the user a gripping element with a manual device actuator to selectively expand or retract the spreading assembly (16) of the present teachings in much the same way as the other embodiments of the handle assembly (12).

Each of the alternative handle assembly embodiments discussed herein when manually operated by a user results in the movement of the actuating arm (46) within the sleeve (44) such that the spreading assembly (16) is expanded so as to manipulate tissue.

Figure 7A:
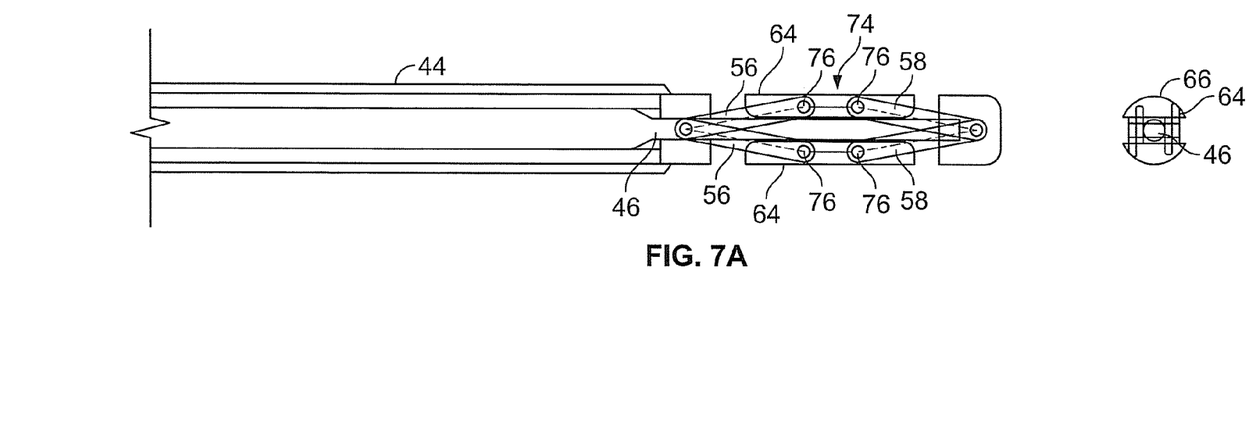
FIGS. 7A-B show a side and end view of a third embodiment of the device of the present teachings in a closed (A) and open (B) position.
Figure 7B:
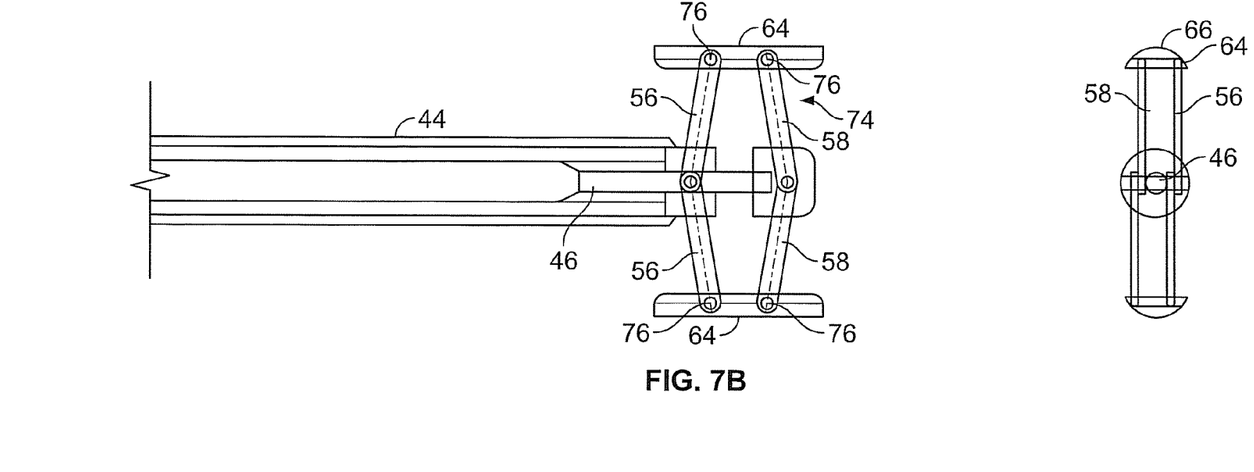
Figure 8A:
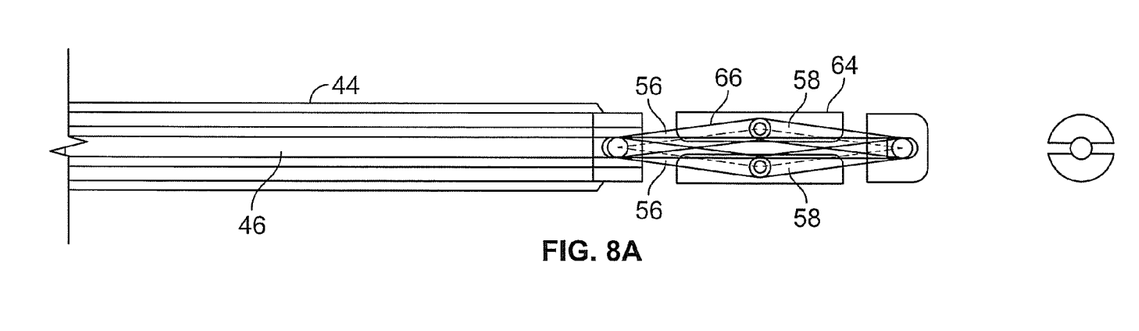
FIGS. 8A-B show a side and end view of a fourth embodiment of the device of the present teachings in a closed (A) and open (B) position.
Figure 8B:
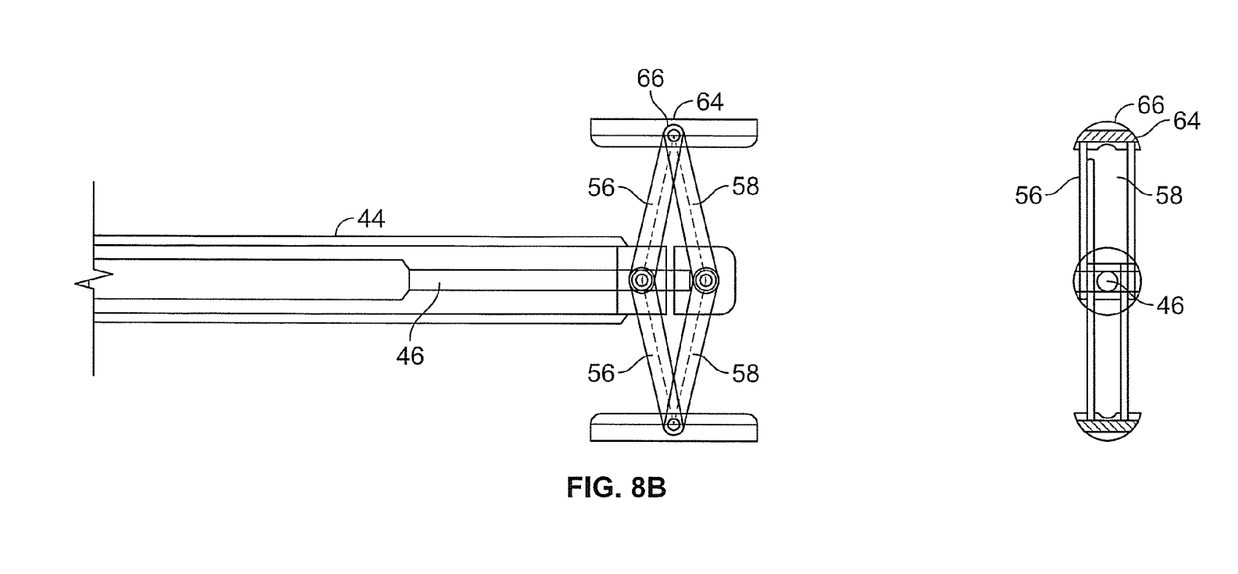

As best shown in FIGS. 7A-B and 8A-B, additional alternative embodiments of the present teachings can be provided which employ the same concept of the earlier described embodiment with the modification of providing a dual-scissor assembly, generally shown at (74), that permits the use of two bracing members (58) pivotally attached to the actuating arm (46) at the proximal end and pivotally attached at a base plate pivot point (76). In FIGS. 8A-B, an alternative embodiment using two bracing members (58) attached at a single base plate pivot point is shown in both the closed (A) and open (B) positions. In FIGS. 7-A-B, the alternative embodiment is shown using two bracing members (58) attached at two distinct pivot points (alternative embodiments provide a configuration with the potential for increased leverage strength during the opening of the spreading assembly (16) as well as, in the case of FIGS. 7A-B, a broader base of support for the base plate (64).

Figure 9:
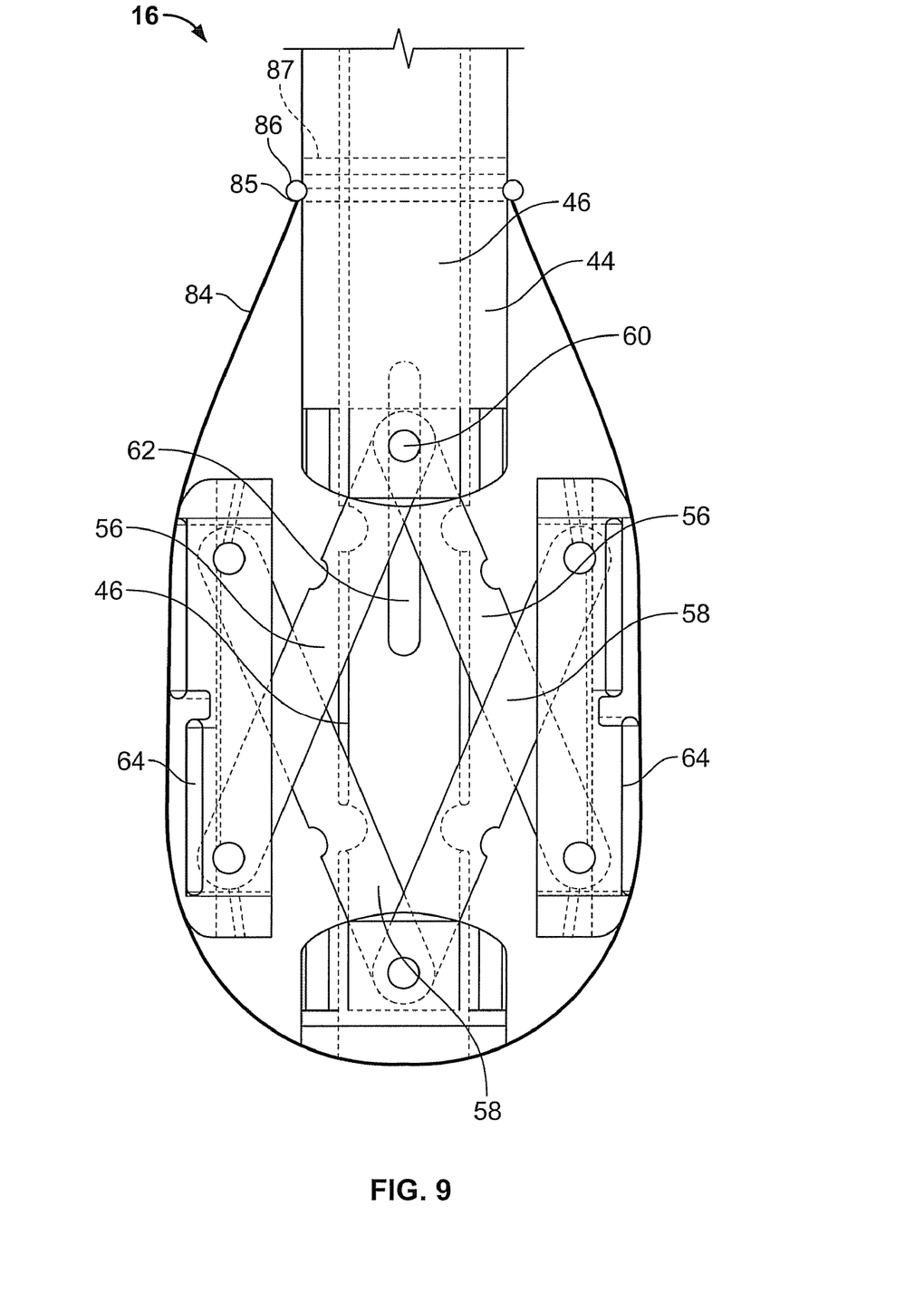
FIG. 9 shows a protective sheath enclosing another alternative embodiment of the spreading assembly of the present teachings.

The present teachings provide a means of protecting the mechanism of the spreading assembly (16) from unwanted contact, entanglement, and interference with the tissue of a subject. On ingress, during operation, and on egress from the tissue-manipulation site within a subject, it is possible for surrounding tissue or bone to become so involved with the internal mechanism of the spreading assembly (16) that the device might be operationally impaired or rendered inoperable altogether. As shown in FIG. 9, the present teachings provide a protective sheath (84) constructed of a highly flexible, high memory material that tightly and closely overlays the entirety of the spreading assembly (16) so as to provide a protective layer capable of keeping all unwanted tissue contact from the working mechanism of the spreading assembly.

The sheath (84) can be constructed of any medically/surgically acceptable elastic formulation that can be easily stretched during full expansion of the spreading assembly (16) without losing its integrity and without causing extreme resistance to spreading and back pressure on the spreading assembly. Further, the material used to fabricate the sheath (84) will have extremely good memory, that is shape-recovery character, and as the spreading assembly is returned to its compact, non-spread configuration, the sheath will return to its tight, close relationship to the more compact configuration of the spreading assembly (16). Thus, the sheath (84), upon spreading of the spreading assembly (16), will provide protection of the mechanism and, upon return to the non-spread configuration the sheath (84) will provide a smooth tight surface around the spreading assembly so as to facilitate the easy passage of the spreading assembly from the subject when the user chooses to retract the device. The sheath (84) can be manufactured of a polyurethane material and will be circumferentially bonded to the sleeve (44) of the device at a bonding point (85) just before the spreading assembly (16) exit from the sleeve (44). In either embodiment, the sheath (84) bonded to the sleeve (44) or bonded to the actuating arm (46), the mechanism of bonding can be by any secure and permanent means known in the art to include, but not limited to using adhesives, heat sealing, shrink film adhesion, or mechanical connection, such as, for example a groove and circumferentially inserted securing ring (86). Alternatively, the sheath (84) can be bonded to the spreading assembly at a point just before the spreading mechanism of the spreading assembly (16). For those embodiments of the present teachings, where the spreading assembly can be released from the actuating arm and left within the subject as a structural support for the bone that that has been manipulated, the device can be configured to have a quick disconnect (87) point between the actuating arm (46) and the spreading assembly (16). Such a quick disconnect can be provided by mechanical disconnect means, manufacture of a programmed break-away or shear point for a given torque, or any method of providing such a disconnection as is known in the art. The sheath (84) for such an embodiment remains intact and in place around the spreading assembly (16).

The alternative configuration of the spreading assembly (16) shown in FIG. 9 is similar in design and assembly to that earlier described in FIGS. 7A and 7B with the adjustment that the two extending arms (56) and the two bracing members (58) cross over each other respectively in a scissor-jack configuration. Each of the ends of the extending arms (56) and bracing members (58) terminate on two attachment points on the buft plate (64) in the same manner as the spreading assembly (16) embodiment shown in FIGS. 7A and 7B.

Each of the embodiments described above are provided for illustrative purposes only and it is within the concept of the present teachings to include modifications and varying configurations without departing from the scope of the present teachings that is limited only by the claims included herewith.

What is claimed is:

1. A surgical apparatus comprising:
    a handle structure including a handle locking structure, the handle locking structure including a handle locking arm and a locking catch;
    a shaft structure having a longitudinal axis, the shaft structure coupled to the handle structure, the shaft structure including a sleeve and an actuating arm movable relative to the sleeve by the handle structure;
    a spreading structure releasably coupled to the shaft structure, the spreading structure including first and second elongated bracing members and first and second elongated extending members, the first and second bracing members and the first and second extending members pivotably interconnected such that the spreading structure is movable by the actuating arm between a compact configuration for insertion into tissue and an expanded configuration in which the bracing members and the extending members are radially displaced relative to the longitudinal axis for manipulating tissue; and
    a protective sheath of shape-recovery material, the protective sheath covering the entire spreading structure in a substantially form fitting manner in any configuration of the spreading structure including the compact configuration, the expanded configuration and any configurations therebetween.

2. The surgical apparatus of claim 1, further including first and second plates within the protective sheath, the first plate pivotably connected to the first bracing and extending members and the second plate pivotably connected to the second bracing and extending members.

3. The surgical apparatus of claim 2, wherein the first bracing member and the first extending member are pivotably connected to different points of the first plate.

4. The surgical apparatus of claim 2, wherein the first bracing member and the first extending member are pivotably connected to the same point of the first plate.

5. The surgical apparatus of claim 1, wherein the handle structure includes first and second pivotably coupled handle members and a controlled compression structure operable to fine-tune the compression of the first and second handle members.

6. The surgical apparatus of claim 5, wherein the compression structure includes a threaded compression shaft rotatably coupled to one of the first and second handle members and slidably passing through a slot of the other of the first and second handle members.

7. The surgical apparatus of claim 5, wherein the compression shaft terminates at a manually controlled stop.

8. The surgical apparatus of claim 7, wherein the handle structure includes a grip stabilizing member extending from one of the first and second handle members.

9. The surgical apparatus of claim 1, wherein the protective sheath is coupled to the spreading structure such that the protective sheath remains with the spreading structure when the spreading structure is selectively released from the shaft structure.

10. The apparatus of claim 1, wherein the protective sheath is made of polyurethane material.

11. The apparatus of claim 1, wherein the handle structure is releasably coupled to the shaft structure.

12. The apparatus of claim 1, further comprising a locking mechanism for releasably locking the spreading structure in the expanded configuration.

13. The apparatus of claim 1, wherein the spreading structure includes a guide bar, the guide bar slidably movable in a guide slot of the sleeve for controlling an amount of radial extension of the spreading structure.

14. A surgical apparatus comprising:
a handle structure including first and second handle members pivotably coupled at a pivot and a threaded compression shaft rotatably coupled to one of the first and second handle members and slidably passing through a slot of the other of the first and second handle members, the compression shaft not passing through the pivot;
a shaft structure having a longitudinal axis, the shaft structure releasably coupled to the handle structure, the shaft structure including a sleeve and an actuating arm movable within the sleeve by the handle structure;
a spreading structure releasably coupled to the shaft structure, the spreading structure including a plurality of elongated members, the elongated members pivotably interconnected such that the spreading structure can be moved by the actuating arm between a compact configuration for insertion into tissue and an expanded configuration in which the elongated members are radially displaced relative to the longitudinal axis for manipulating tissue; and
a protective sheath of shape-recovery material, the protective sheath covering the entire spreading structure in a substantially form-fitting manner in any configuration of the spreading structure, including the compact configuration, the expanded configuration and any configurations therebetween.

15. The apparatus of claim 14, wherein the spreading structure includes a guide bar, the guide bar slidably movable in a guide slot of the sleeve for controlling an amount of radial extension of the spreading structure.

16. The apparatus of claim 14, further comprising a locking mechanism for releasably locking the spreading structure in the expanded configuration.

17. The apparatus of claim 14, further including first and second plates within the protective sheath, the first and second plates pivotably connected with the elongated members.

18. The apparatus of claim 17, wherein the plurality of the elongated members are crosswise coupled between the first and second plates.

19. The apparatus of claim 17, wherein the first and second plates are parallel in both the compact and expanded configuration.

20. A surgical apparatus comprising:
a handle structure including first and second handle members pivotably coupled at a pivot and a threaded compression shaft rotatably coupled to one of the first and second handle members and slidably passing through a slot of the other of the first and second handle members, the compression shaft not passing through the pivot;
a shaft structure having a longitudinal axis, the shaft structure releasably coupled to the handle structure, the shaft structure including an actuating arm movable by the handle structure; and
a spreading structure releasably coupled to the shaft structure, the spreading structure including a plurality of elongated members, the elongated members pivotably interconnected such that the spreading structure can be moved by the actuating arm between a compact configuration for insertion into tissue and an expanded configuration in which the elongated members are radially displaced relative to the longitudinal axis for manipulating tissue.

21. The surgical apparatus of claim 20, further comprising a protective sheath of shape-recovery material, the protective sheath covering the entire spreading structure in a substantially form-fitting manner in the compact configuration and the expanded configuration.

* * * * *